(12) United States Patent
Rose et al.

(10) Patent No.: US 7,348,027 B2
(45) Date of Patent: Mar. 25, 2008

(54) TASTE MASKED VETERINARY FORMULATION

(75) Inventors: John Rose, Blue Springs, MO (US); Jochem Rueter, Shawnee, KS (US)

(73) Assignee: Bayer Healthcare LLC, Tarrytown, NY (US)

( * ) Notice: Subject to any disclaimer, the term of this patent is extended or adjusted under 35 U.S.C. 154(b) by 0 days.

(21) Appl. No.: 11/102,426

(22) Filed: Apr. 8, 2005

(65) Prior Publication Data

US 2006/0228399 A1    Oct. 12, 2006

(51) Int. Cl.
*A61K 31/495* (2006.01)
*A61K 9/26* (2006.01)

(52) U.S. Cl. .............. 424/470; 424/438; 424/442; 514/250

(58) Field of Classification Search ........ 424/489; 435/118
See application file for complete search history.

(56) References Cited

U.S. PATENT DOCUMENTS

| | | | | |
|---|---|---|---|---|
| 3,466,362 A | * | 9/1969 | Schlegel et al. ........ | 424/489 |
| 5,824,336 A | * | 10/1998 | Jans et al. ........... | 424/441 |
| 5,945,317 A | * | 8/1999 | Byrne et al. .......... | 435/118 |
| 2002/0012701 A1 | * | 1/2002 | Kolter et al. ......... | 424/468 |
| 2004/0096499 A1 | * | 5/2004 | Vaya et al. ........... | 424/468 |

FOREIGN PATENT DOCUMENTS

| | | | |
|---|---|---|---|
| GB | 2252730 | * | 8/1992 |
| WO | WO 01/35925 | * | 5/2001 |
| WO | WO 01/37808 | * | 5/2001 |

* cited by examiner

*Primary Examiner*—Neil S. Levy
(74) *Attorney, Agent, or Firm*—Jessica Monachello

(57) ABSTRACT

A method of producing a self-take anthelmintic that includes active components that are undesirable to at least one sense of a target animal. The active ingredients including praziquantel are mixed with artificial beef and yeast components and subjected to a first compression. The resulting rough tablet is then ground to increase the density of the material by approximately 100% of the original density. Thereafter, the material is subjected to a second compression to form a final self-take tablet.

9 Claims, No Drawings

TASTE MASKED VETERINARY FORMULATION

FIELD OF THE INVENTION

The invention is directed to a taste masked veterinary oral formulation and methods of producing the formulations.

BACKGROUND OF THE INVENTION

Many veterinary pharmaceuticals and other veterinary formulations include components that taste very bitter or are otherwise distasteful or undesirable to one or more senses of an animal, so that the animal refuses to take the composition orally when offered. Anyone who has ever tried to give medicine to a pet dog or cat knows how difficult the process can be. Dogs and cats do not eat tablets willingly and are highly suspicious of liquids and powders. Their acute sense of smell will often warn them that their owner is approaching with some form of unpleasant medicine even when medicine is hidden in a treat.

Examples of such unpleasant medicines are anthelmintic veterinary formulations containing the active ingredient praziquantel. Praziquantel tastes very bitter and refused by virtually all dogs offered the active ingredient without some type of taste masking. Even with taste masking, in some instances, an animal may take the offered composition in its mouth, but then spit it out once it becomes aware of the bitter taste. Further, sometimes the animal will take the composition when it is first offered to it, but then learns that it has a bad taste, texture or other undesirable trait and will refuse the medicine on subsequent offerings.

Another drawback of praziquantel lies in the dosage size. A single dose of praziquantel may require a large single tablet or two or more regular-sized tablets. A large single tablet is not easily given to a pet, and, once taken, the pet will quickly learn to resist taking the second and subsequent tablets. An animal becomes more and more reluctant to take additional tablets with each subsequent tablet. With some highly unpleasant active ingredients and for a big animal, perhaps as many as ten taste-masked tablets could be required for a therapeutic amount of medicine masked by a sufficient amount of a masking agent to get the animal to take a therapeutic dose. The animal could easily lose interest in taking additional tablets, and an owner could also lose heart. Without proper dosing, the therapeutic purpose of the medicine could be reduced or lost entirely.

Various types of masking agents have been utilized in the past to hide or mask the taste of medicines so that an animal will take it. Sometimes, masking various ingredients by coating them with sufficient neutral or palatable material will encourage the animal to take the offered medicine. However, if the animal bites through the tablet given in this manner, the animal will often discover the undesirable taste and will refuse to consume it. One approach used in pharmaceuticals, microencapsulation, is too expensive for an animal health product.

Animals often perceive whether they like something or not first, and sometimes principally, by smell. The taste and/or texture and chewability or mouthfeel also come into play once the animal has the product in its mouth. With respect to texture and chewability, dogs normally like products that are chewy rather than hard and brittle. Consequently, a self-take veterinary medicine must appeal to the animal's senses of smell and taste, as well as texture and mouthfeel and any other relevant senses in order to entice the animal to take the product in its mouth and then consume it completely. Tablets are especially difficult to administer to dogs because they can be harder and more brittle than other delivery forms.

Taste and smell masking agents have been used to improve the animal's perception of a veterinary medicine by diluting unpleasant active ingredients in a substantial amount of a carrier. The carrier masks or conceals the smell or taste of the unpalatable medicinal component. Dilution of the unpalatable actives can become a problem when large amounts of an active ingredient must be administered to the animal. The large amount of active requires a proportionally large amount of a masking agent to fool an animal's senses. As noted before, some anthelmintic compounds, especially praziquantel, require a fairly large dose of active component to be therapeutically effective and cannot be easily masked with a small amount of a masking agent. To mask such a composition effectively requires a significant amount of masking agent, which, in turn, can make a tablet too large for the animal to take without chewing. This size problem becomes especially difficult when the masking agent is not highly effective in masking the bitter tasting active, thereby requiring an even larger amount of masking agent to be used in the formula.

Tableting machines in the pharmaceutical industry are also designed for conventionally sized tablets, and therefore typical tableting machines are limited in the volume of material that can be handled and produced for a specific tablet size. Such machines cannot handle the large amount of mixed active and masking agent that may be required for many taste-masked tablets. If a very strong compression force is required to force a large amount of material into a single regular size tablet, the tablet may then be too hard and brittle and therefore rejected by the target animal.

The art still needs a tablet and manufacturing process for a large dose veterinary medicine that can be effectively and economically masked by a relatively low amount of a taste or smell masking agent.

SUMMARY OF THE INVENTION

The principal object of the invention therefore is to provide a veterinary composition comprising a medicine and a masking agent.

Another object of the invention is to provide a composition comprising a veterinary composition that can be masked and also provided in a therapeutic dose, without upsetting the animal receiving the veterinary composition.

An additional object of the invention is to provide a composition for masking the taste of praziquantel while maintaining a manageable dose regimen for the animal.

A further object of the invention is to provide a process for making the composition of the invention.

Additional objects and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

Other objects and advantages of this invention will become apparent from the following descriptions set forth, by way of illustration and example, certain embodiments of this invention.

To achieve the foregoing objects and in accordance with the purpose of the invention, as embodied and broadly described herein, the invention provides a method of preparing an oral self-take veterinary formulation. The veterinary formulation includes at least one active component that is undesirable to at least one of the senses of a target animal for the formulation. The method includes the steps of combining the active component and a masking component, which may be a mixture of ingredients that provide taste or scent masking properties, compressing this first mixture to form a crude tablet or slug, grinding the slug to form particles of greater density than the material prior to the first compression, and compressing the formulation a second time to form the final self-take tablet of acceptable hardness.

An advantage of the invention is that when the active ingredient is praziquantel, an especially difficult medicine, the masking material may be a commercial mixture of artificial beef flavor plus yeast and other ingredients necessary for manufacturing a solid dosage form by a compression process.

DETAILED DESCRIPTION OF THE PREFERRED EMBODIMENTS

Reference will now be made in detail to the presently preferred embodiments of the invention.

The present invention is directed to a self-take oral veterinary formulation and methods of producing the formulation. The formulation comprises at least one active ingredient (preferably more than one and even more preferably at least three active ingredients) and at least one masking agent. At least one of the active ingredients of the formulation may be very bitter or otherwise undesirable to at least one sense of a target animal. Surprisingly, the masking agent has proven particularly useful with a formulation comprising a plurality of active ingredients, allowing tablets made from the formulation to be of a small enough size to minimize the amount of tablets that must be administered to the target animal. The method for making the tablet comprises two compression steps to produce the formula: first compression to make the material more dense and a second compression step to form the self-take tablet.

The active ingredients of the formulation may be for any of a variety of medical or physical improvements of the target animal wherein it is desirable to provide the animal with a therapeutic or effective dosage of the formulation, with the minimal number of individual tablets possible. A preferred formulation to be provided under the invention is an anthelmintic for ridding the target animal of certain parasites. A more specific preferred formulation is an anthelmintic formulation for de-worming a target animal's intestines with a combination of praziquantel and a tetrahydropyrimidine such as pyrantel and a benzimidazole such as febantel. Such anthelmintic combinations are extensively described in U.S. Pat. No. 5,036,069 to Andrews et al., issued Jul. 30, 1991 which is incorporated herein by reference. Other anthelmintics that may be useful in the invention include avermectin, ivermectin, moxidectin, milbemycin and other macrolide anthelmics.

Anthelmintic formulations of the invention include a therapeutic dose of praziquantel that the target animals, especially dogs, find undesirable to the sense of smell or taste. Further, dogs may find the texture, hardness or some other attribute of a conventional tablet undesirable to the senses of the animal.

Anthelmintics, especially those noted above, often require a comparatively high dose of one or more actives to provide an effective dose. However, where the quantity of required active is high and the taste or smell is especially offensive to the target animal, sufficient dilution by methods of the prior art produce tablets that are too large for the target animals or require a large number of tablets in order to get a therapeutic or desired effect. A dog may be fooled by the first tablet but not with the second or third tablet.

Preferred actives in accordance with the invention are: Febantel (CAS No. 58306-30-2), Praziquantel (CAS No. 55268-74-1), and Pyrantel (CAS No. 22204-24-6). These endoparasitizides are used with dogs. Praziquantel kills mature and immature development stages of tapeworms in the intestine after a single treatment. Within a few seconds of a tapeworm coming into contact with praziquantel its interaction with phospholipids and proteins causes damage to the tegument of the tapeworm. The subsequent inflow of calcium ions causes an immediate contraction of the entire strobila. Moreover, these changes lead to a reduction of glucose intake and an accelerated depletion of energy reserves of the tapeworm.: Pyrantel, also known as pyrantel embonate, is an anthelmintic of the tetrahydropyrimidine group of compounds, and acts in a similar way to levamisol, by inducing a depolarising neuromuscular blockade. Pyrantel, being a cholinergic agonist, acts as an excitatory neurotransmitter at the nicotinergic receptor causing spastic paralysis of the parasite. The mode of action of febantel is primarily based on interference with the carbohydrate metabolism of the parasitic worm. The resulting suppression of mitochondrial reactions (inhibition of fumarate reductase) and interference with glucose transport acts not only on all developmental stages of the helminths but also on the eggs containing the larvae. Benzimidazoles bind to the structural protein tubulin, thereby preventing its polymerization to microtubules that provide the transport system for the absorbing cells. The consequence of blocking this transport activity is incomplete absorption and digestion of nutrient particles and cellular autolysis through activation of lysosomal enzymes.

The combination of these three ingredients is marketed currently as DRONTAL PLUS, and the combination possesses an extremely wide spectrum of activity. Its is used to treat infestation by dog roundworms and tapeworms including: *Toxocara canis, Toxascaris leonina, Uncinaria stenocephala, Ancylostoma caninum, Echinococcus granulosus, Echinococcus multilocularis, Dipylidium caninum, Taenia* spp., *Multiceps multiceps, Mesocestoides* spp., and *Trichuris vulpis* (whipworms).

Drontal Plus tablets are fed directly to an animal preferably concealed in a piece of meat, cheese, or tidbit or, poked directly down the throat of the animal. No special dietary measures are required either in adult dogs or in pups. The product is given in a single administration and need not be administered over several days. The dosage is one tablet per ten kilograms of body weight. For many large (and not so large) dogs, the number of required tablets can be a problem. A basset hound (40-60 lbs) will need two to three tablets, a golden retriever (60-80 lbs) will need three to four tablets, and a Bernese mountain dog (88-97 lbs) will need four to five tablets.

The preferred taste masking agent is a combination of yeast and an artificial beef flavor. The most preferred artificial beef flavor is supplied by Pharm Chemie, Inc., 1877 Midland Street, Syracuse, Nebr. 48666. The company reports that it has developed immediate release oral anthelmintic suspensions. The preferred flavor is identified as PC-0125. This flavor is a hydrolyzed vegetable protein and so is free of Bovine Spongiform Encephalopathy (BCE) and hoof and mouth disease (HMD) contamination.

The masking agent of the invention is preferably a mix of an artificial beef flavor component and a yeast component. These masking agents are mixed with the active ingredient or ingredients and other, conventional, inert ingredients used in producing tablets. This mixture, especially when treated as set forth below, produces a formulation that will be accepted by a relatively high percentage of target dogs, and the dogs will not reject later doses. Artificial beef flavor and yeast were found to be effective to mask a very large amount of active ingredient, especially in a formulation having an effective dosage of praziquantel in combination with pyrantel and febantel. In this manner, relatively high doses of active ingredients, for example in the range of from about fifteen percent to about thirty percent by weight, can be masked and given as a self-take oral tablet without forcing the animal to take the tablet and without requiring a large amount of tablets to be given.

The tablet of the invention is made by mixing the initial combination of ingredients, compressing the resulting mixture into crude tablet bodies ("slugs"), followed by grinding the slugs and compressing again into the final tablet shape. Slugging is conventionally used in the pharmaceutical industry to enhance content uniformity or homogeneity of a tablet formula. In the present invention, slugging is not used primarily to achieve uniformity, but also to increase density, thereby allowing manufacture of acceptable tablet size. The method of the invention thus comprises the step of producing a comparatively dense material that can be further compressed into a smaller self-take tablet. This double compressed tablet can be taken orally by an animal in a full therapeutic dose with as few tablets as possible. Further, it is desirable and, within the invention, possible for the completed tablet to have texture and chew characteristics that target animals are likely to find favorable when the formulation is given routinely on a self-take basis.

In the method of the invention, the components of the formulation, including the active, and the artificial beef and the yeast components are thoroughly mixed. Preferably, the artificial beef and yeast components comprise from about 20% by weight to about 35% by weight, and more preferably about 30% by weight of the total tablet weight. Also, the artificial beef component may preferably be present in a ratio of up to about 5 parts by weight to about 1 part by weight to the yeast component, and more preferably in a ratio of up to about 2 parts to 1 part by weight. The artificial beef component can be produced from various tissues of animals, preferably livers of animals including, but not limited to beef, chicken, pork and lamb together with other ingredients and further, may include artificial flavors, freeze dried or desiccated or otherwise suitably rendered for a dry formulation. The yeast may be any commercially available yeast normally used as a flavor enhancer or otherwise that is acceptable for use with the target animals.

The volume of the formulation with artificial beef and yeast components added and a high percentage of active is often too large to fit into tablet forming chambers of a conventional tablet press for the tablet size desired. It has been found in accordance with the invention that the composition of the formulation can be first compressed, in a conventional tablet press to form a crude tablet or slug. Preferably, the first compression is made with a pressure that increases the density of the original mixture substantially but leaves some elasticity for a subsequent second compression. In this manner, the mixture is compressed or slugged into a first composition having a resultant density substantially more dense than the density of the original formulation (for example, about 75% to about 125% greater) with a corresponding volume substantially smaller than the original mixture.

The resultant crude tablets comprising the first composition are then ground into particles, sieved, preferably to a screen mesh size of from about 12 to about 16 mesh, as determined by manual sieves, with the individual particles being more dense than the first compressed composition. As a consequence of this first compression the resultant particles are not only relatively highly homogenous but also surprisingly much denser thereby allowing the necessary volume of tableting mixture to fit into the tablet press chamber and pressed into a tablet of the desired size. This reduction in overall tablet size allows the addition of large amount of masking material and production of an acceptable size tablet.

The first composition is then processed and delivered to a tablet press which may be the same or different from to the original compression apparatus. Preferably, less pressure is applied in this second compression, so that the resulting tablet is not as hard and is more chewable in comparison to the conventional tablets. Tablets of different size may be made for different sized animals; however, it is preferred that an entire dosage for each of the target animals is contained in as few tablets as possible.

The invention may be further illustrated by the following example. Specific examples are not intended to be limiting, but are only intended to help teach one skilled in the art to understand some features of the invention.

EXAMPLE 1

Two batches of an anthelmintic formulation mixture were prepared having the following composition:

TABLE 1

Formulations of Example 1

| Approximate Weight Percent | Batch 1 (grams) | Batch 2 (grams) | Ingredient |
|---|---|---|---|
| 3% | 75 | 60 | Praziquantel |
| 8.72% | 218 | 174.2 | Pyrantel Pamoate |
| 15% | 377.75 | 300 | Febantel |
| 16% | 400 | 320 | Microcrystalline Cellulose (Tableting aid) |
| 23.2% | 579.25 | 465.80 | Lactose monohydrate (Texturing Agent) |
| 20% | 500 | 400 | Artificial Beef Flavor |
| 10% | 250 | 200 | Yeast |
| 2% | 50 | 40 | Silicon Dioxide - fumed (Flow agent) |
| 1% | 25 | 20 | Magnesium Searate |
| 1% | 25 | 20 | Stearic Acid (Lubricant) |
| 100% | 2500 | 2000 | TOTAL |

All the components for each batch (except the magnesium stearate and the stearic acid) were mixed in a P/K blender for five to ten minutes. The resulting powder was then screened through a #12 mesh screen and returned to the P/K blender. The powder was then mixed for another five to ten minutes. The magnesium stearate and stearic acid were screened through a #60 mesh screen and added to the blender. Mixing was then continued for two minutes. This finished powder was then slugged into 1.2-1.5 gram tablets. These tablets were then ground and put through a #16 mesh screen and mixed in the P/K Blender for five minutes. Compressed tablets were then made in dog bone shapes in three sizes: 760 milligram tablets (for small dogs), 2.28 gram tablets for medium dogs, and 4.56 gram tablets (for large dogs).

EXAMPLE 2

Physical properties for a third batch manufactured according to the formula of Example 1 were measured at various points during the manufacturing process. After mixing in the P/K blender for the first time, the powder had a density of 0.32 g/ml, good flowability and an angle of repose of 27 degrees. Angle of repose was measured by pouring 100 grams of material through a funnel on to a glass plate approximately three and one-half inches below the funnel mouth. A "tap density" was measured as 0.36 g/ml. "Tap density" was determined by placing the powder in a graduated cylinder and then tapping the graduated cylinder three times on the table before measuring the density.

After slugging, the slugs had a slug weight of about 1.2-1.5 grams and a hardness of 8-12 KG.

After the slugs had been ground and mixed again in the PK mixer, the resulting powder was sieved to measure particle size. The particle size distribution set forth in Table 2 was obtained

TABLE 2

Particle Size Distribution in Example 2

| Screen Size | Percent Retained |
|---|---|
| #12 | 0.6% |
| #20 | 32.4% |
| #30 | 10% |
| #40 | 10.7% |
| #60 | 10.4% |
| #100 | 12.4% |
| #200 | 8% |

The powder comprising the reground slugs had a density of 0.77 g/ml, a tap density of 0.79 g/ml and an angle of repose of 29 degrees.

The powder was then formed into tablets as described above. The hardness of the small and medium sized dog bone tablets was determined to be 8-11 KG.

EXAMPLE 3

A total of 74 dogs were included in a field study to evaluate the acceptance and palatability of artificial beef flavored tablets prepared in accordance with the invention. Tablets were offered to the dogs one time by their owners in their homes. The dogs were characterized by their owners before the test as "eats almost anything" (52 dogs), "somewhat selective eater" (16 dogs), "very selective eater" (5 dogs), with one dog being identified as a "somewhat selective/very selective eater."

Sixty four of seventy four dogs (86.5%) consumed the full complement of tablets within one minute, 2 dogs partially consumed the tablets, 6 dogs sniffed and licked the tablets but did not eat them, and 2 dogs showed no interest in the tablets. All 10 of the dogs that did not finish the tablets within one minute had been characterized as "somewhat" or "very selective" eaters.

EXAMPLE 4

A crossover test was used to determine the acceptability of tablets according to the invention compared to Heartgard® Chewable tablets. Heartgard® Chewable tablets use ivermectin as an active ingredient, which tastes less offensive than praziquantel and is administered in much lower amounts. Fifty small dogs and 100 large dogs were fed tablets on an approximately weekly basis according to a pre-determined schedule. The number of tablets or the size of the chewable formulation offered was dependent on body weight of the dog. The tablets were offered by their owners to non-fasting dogs, and the number of tablets consumed within a period of 60 seconds was recorded. Treatment was scored a failure if less than the entire dose was consumed within the 60 seconds. Palatability scores, as a percent of dogs with successful treatment, are set forth below for several test iterations.

TABLE 3

Palatability Scores for Invention and Commercial Product

| Dog Size | Palatability Score (invention) | Palatability Score (commercial product) |
|---|---|---|
| Large | 78%, 78%, 82% | 96% |
| Small | 64%, 74%, 66% | 93% |

These results show a marked improvement in palatability of the invention, especially considering the difference in the flavors of the praziquantel of the tablets of the invention and the Ivermectin of the commercial product.

The purpose of the above description is to illustrate some embodiments of the present invention without implying a limitation. It will apparent to those skilled in the art that various modifications and variations may be made in the apparatus or procedure of the invention without departing from the scope or spirit of the invention.

What is claimed is:

1. A method of preparing taste masked veterinary formulation wherein said formulation includes at least one active component that is undesirable to at least one of the senses of a target animal for the formulation, said method comprising the steps of:
   a. providing at least one active component, wherein said active component comprises at least one anthelmintic active ingredient;
   b. providing at least one masking agent, wherein said masking agent comprises a mixture of ingredients that provide taste masking properties;
   c. mixing together said active component and said masking agent to form a mixture;
   d. subjecting said mixture to a first compression to form a slug;
   e. grinding said slug to form particles having a density of at least about 75-100% greater than the particles of said mixture; and
   f. subjecting said particles to a second compression to form a final taste masked tablet.

2. The method of claim 1, wherein said masking agent is a mixture of an artificial beef component and a yeast component.

3. The method of claim 2, wherein said mixture comprises by weight:
   a. about 21% by weight of said anthelmintic active ingredient;
   b. about 10-30% by weight of said artificial beef component, and
   c. about 5-15% of said yeast component, wherein the ratio of artificial beef component to yeast component is about 2 to 1.

4. The product produced by the method of claim 3.

5. A bone shaped tablet made by the method of claim 3.

6. A method of preparing a self-take anthelmintic veterinary formulation, comprising:

a. providing an anthelmintic active ingredient comprising a therapeutic dosage of praziquantel;
b. providing a masking composition including a yeast component and an artificial beef component effective in eliciting self-take behavior in dogs to which the formulation is offered;
c. mixing together said anthelmintic active ingredient and said masking composition to form a basic mixture;
d. subjecting said basic mixture to a first compression to form a slug;
e. grinding said slug to form particles of greater density than said basic mixture; and
f. subjecting said particles to a second compression to form a final taste masked tablet.

7. The method of claim 6, wherein said masking composition includes said artificial beef component in a range between one and five parts by weight to one part by weight yeast component.

8. The method of claim 7, wherein said masking component includes said artificial beef component in a range of about two parts by weight to one part by weight of said yeast component.

9. The method of claim 7, wherein said anthelmintic active ingredient further comprises therapeutic doses of pyrantel pamoate and febantel.

* * * * *